(12) United States Patent
Steiner et al.

(10) Patent No.: US 6,817,746 B2
(45) Date of Patent: Nov. 16, 2004

(54) OPTICAL DISTRIBUTION COMPONENTS

(75) Inventors: Ivan B. Steiner, Ridgewood, NJ (US); Robert J. Saccomanno, Montville, NJ (US)

(73) Assignee: Honeywell International Inc., Morristown, NJ (US)

(*) Notice: Subject to any disclaimer, the term of this patent is extended or adjusted under 35 U.S.C. 154(b) by 81 days.

(21) Appl. No.: 10/167,367

(22) Filed: Jun. 10, 2002

(65) Prior Publication Data

US 2003/0012533 A1 Jan. 16, 2003

Related U.S. Application Data

(60) Provisional application No. 60/297,387, filed on Jun. 11, 2001.

(51) Int. Cl.[7] .................................................. F21V 7/04
(52) U.S. Cl. .................. 362/556; 362/84; 362/583; 362/292; 362/582; 362/293; 362/230; 362/554; 362/428; 362/385; 362/233
(58) Field of Search ............................... 362/556, 84, 2, 362/252, 583, 292, 582, 293, 262, 230, 554

(56) References Cited

U.S. PATENT DOCUMENTS

| | | | |
|---|---|---|---|
| 5,217,285 A | * 6/1993 | Sopori | ........................... 362/1 |
| 5,799,126 A | 8/1998 | Nagatani et al. | |
| 5,900,982 A | * 5/1999 | Dolgoff et al. | ............. 359/619 |
| 5,967,653 A | 10/1999 | Miller et al. | |

* cited by examiner

Primary Examiner—Stephen Husar
Assistant Examiner—Bertrand Zeade
(74) Attorney, Agent, or Firm—Kurt A. Luther; James W. Falk; Philip Kirkpatrick

(57) ABSTRACT

An efficient redundant light distribution system includes redundant light generation enclosures providing light to a collector array 10, coupled to an ultraviolet to red converter 20, a combination array 30, a distribution array 40 and multiple projection lenses 4.

17 Claims, 7 Drawing Sheets

OPTICAL DISTRIBUTION COMPONENTS

This application claims the benefit of U.S. Provisional Application No. 60/297,387, filed Jun. 11, 2001, which is herein incorporated by reference in its entirety.

BACKGROUND OF THE INVENTION

1. Technical Field

The present invention relates to non-imaging optics, and more particularly to the distribution of illumination light using fiber optics.

2. Background Art

There are many applications for which it desired (or required) to have redundant sources of light. For example, the backlight for an aircraft cockpit display may require two separate light sources. If one of these should fail, the other one would provide backup illumination. Of course this could be accomplished by means of a moving mechanism that moves the failed light source out of the way while the operational one is moved into position to replace it. However, moving mechanisms add complexity, expense, increased space requirements, and reliability concerns. In addition, it may be intolerable to have even the short period of display dead time that would be required to change light sources.

There is a long felt need for a compact light generation and light distribution system that delivers cool, low angular divergence light to a large number of remote sites, such as aircraft displays, with a high light flux transmission efficiency.

SUMMARY OF THE INVENTION

A light distribution system has been developed to distribute cool light from a central light generation enclosure to a plurality of remote locations. More specifically, the light distribution system distributes light from one or more light generation enclosures (LGE), where each LGE includes a high intensity discharge (HID) lamp. An LGE can be exceptionally compact in relation to the power of the enclosed lamp. This compactness derives from the small volume mirror enclosure of a lamp centered within the enclosure.

A system according to the present invention may include a collection array, an ultraviolet to red converter, a combination array and a distribution array. Each of these components may be based on the use of the solid core optical fiber conduits and non-imaging optical morphing elements. The light transmitted by these solid core optical fiber conduits feed a plurality of morphing optical elements that may be made of glass, plastic, or any other suitable light transmitting optical medium, which morphing elements collimate the light they propagate and project the light beams from the morphing elements into object space. The projected beams illuminate one or more targets or feed one or more optical devices such as, for example, luminares.

The light from the LGE propagates through the light distribution system with exceptionally high efficiency and projects from it with exceptionally low angular divergence. This high efficiency results from optical designs morphing optical elements, the efficiency of solid core plastic optical fiber conduits, and the accurate sizing and coupling methodology implemented at the interfaces between adjacent elements. In accordance with an aspect of the invention, the morphing optical elements that are fed by light from the optical fiber conduits are structured to obtain low angular divergence. Specifically, the morphing optical elements have small circular input port apertures and large exit port apertures, thereby forming a plurality of collimator elements that project light beams having low angular divergence. Compared with light beams having high angular divergence, the low angular divergence light beams are more easily shaped, concentrated, and/or otherwise controlled thereby minimizing wasted light.

DETAILED DESCRIPTION OF THE INVENTION

Figure 1:
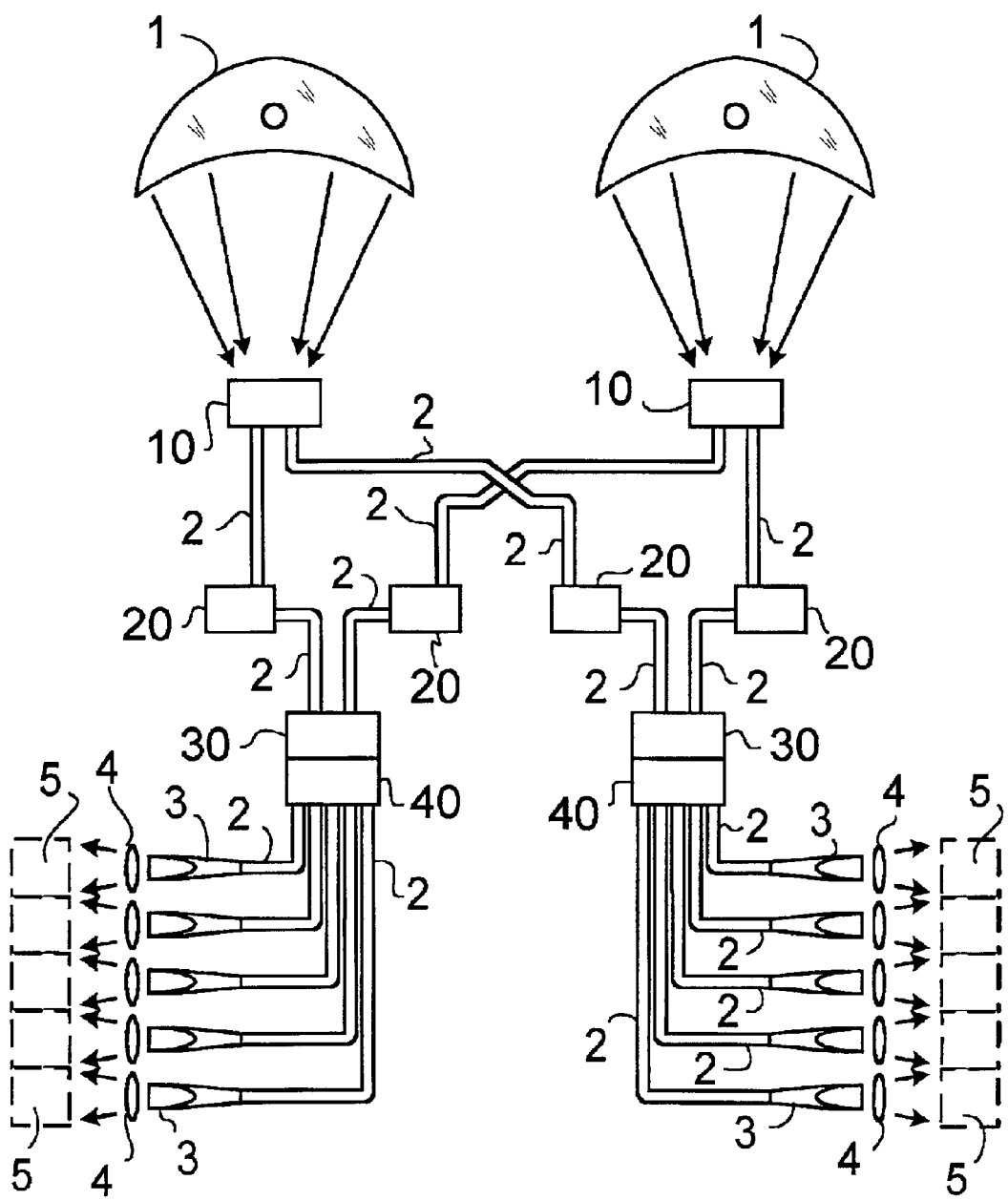
FIG. 1 is a block diagram of a light distribution system incorporating various optical distribution components in accordance with an illustrative embodiment of the present invention.

Referring first to FIG. 1, a light distribution system, using components in accordance with the present invention, is illustrated. Two light generation enclosures (LGE) 1 project light into two respective collector arrays 10. Light is gathered in each collector array 10 and is transmitted, via fiber optic cables 2, to an ultraviolet to red converter 20, where the ultraviolet (UV) portion of the light is converted into red visible light. The ultraviolet to red converter 20 recycles undesirable UV light into visible red light which is typically deficient in a high intensity discharge (HID) lamp.

Light next flows from the ultraviolet to red converter 20 to a combiner array 30. The combiner array 30 allows the light from multiple light generation enclosures 1, such as redundant light generation enclosures 1 that might be found on the left and right sides of an aircraft. The use of a combiner array 30 allows the light distribution system to provide light at each of the output projection lens 4 after the failure of a single light generation enclosure 1.

Light then passes from the combining array 30 to a distribution array 40, which is in close optical contact with the combining array 30. Next, light passes from the distribution array to multiple, for example twenty-five (25) left hand side and twenty-five (25) right hand side, fiber optic cables 2 that are turn connected to multiple optical snouts 3. Finally, light is projected from each optical snout 3 through a projection lens 4 to form a projected image shape 5 such as, for example a square image shape. Such square projected image shapes 5 could be arranged to provide uniform area illumination.

The fiber optic cables 2 may be manufactured from solid core plastic fibers, such as Mitsubishi ESKA acrylic fibers or from glass. Glass is the preferred material when:

(a) higher heat resistance is required at operating temperatures above about 70 Celsius, (b) to obtain improved visible light transmission efficiency at cable lengths exceeding 12 feet, (c) the level of exposure to ultraviolet UV light would degrade the transmittance of plastic solid core fibers, or (d) when bends required in solid core fibers are sharp enough to generate light leakage losses or significant decollimation effects.

Figure 2:
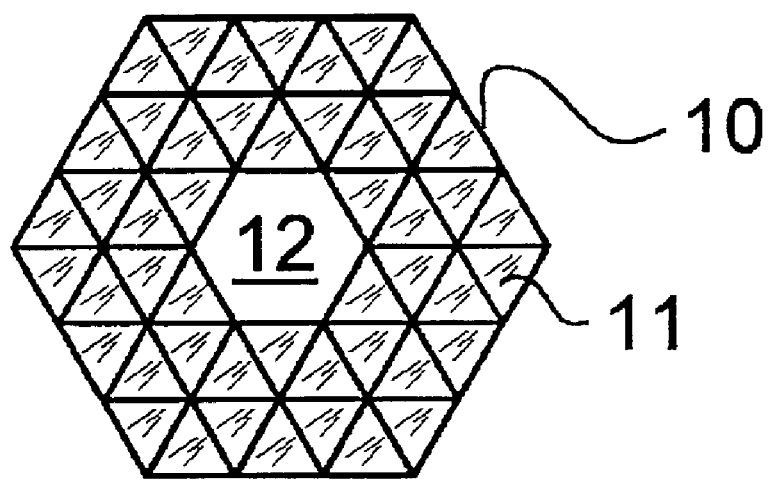
FIG. 2 depicts certain features of a collector array optical component.
Figure 2:
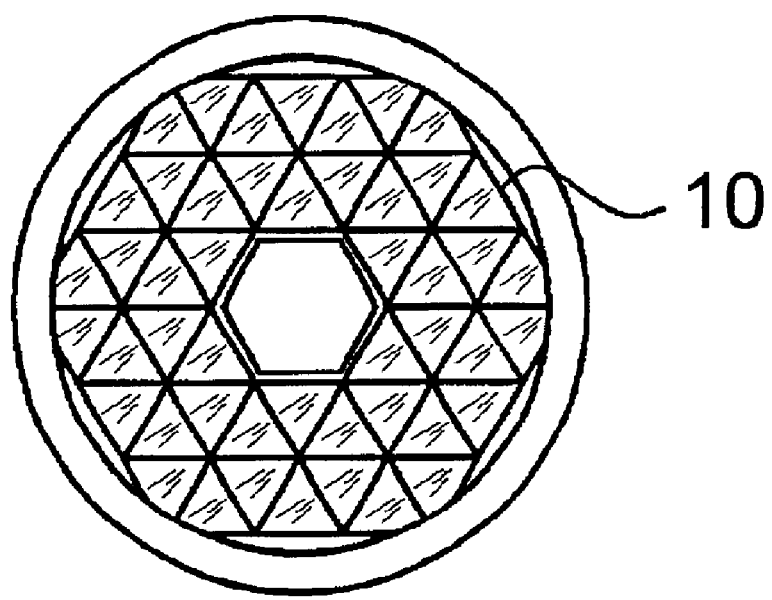

Referring next to FIG. 2, further details of the collector array 10 are shown. Collector array 10 is a hexagonal shaped array that is built up from individual triangular morphing elements 11 surrounding a hollow central region 12. The hollow central region 12 could correspond to the shadow of an HID lamp where the light generation enclosure 1 includes a single parabolic mirror. In an exemplary embodiment, the collector array 10 includes forty-six (46) triangular morphing elements 11, where the light exits the collector array through circular end apertures of each triangular morphing element via fiber optic cables 2.

In one illustrative embodiment, the triangular morphing element 11 includes a uniform cross-section equilateral triangular aperture element region that morphs into conical section. Arrays of such elements can be efficiently packed into arrays without packing fraction losses to feed into multiple fiber optic cables 2.

Figure 3:
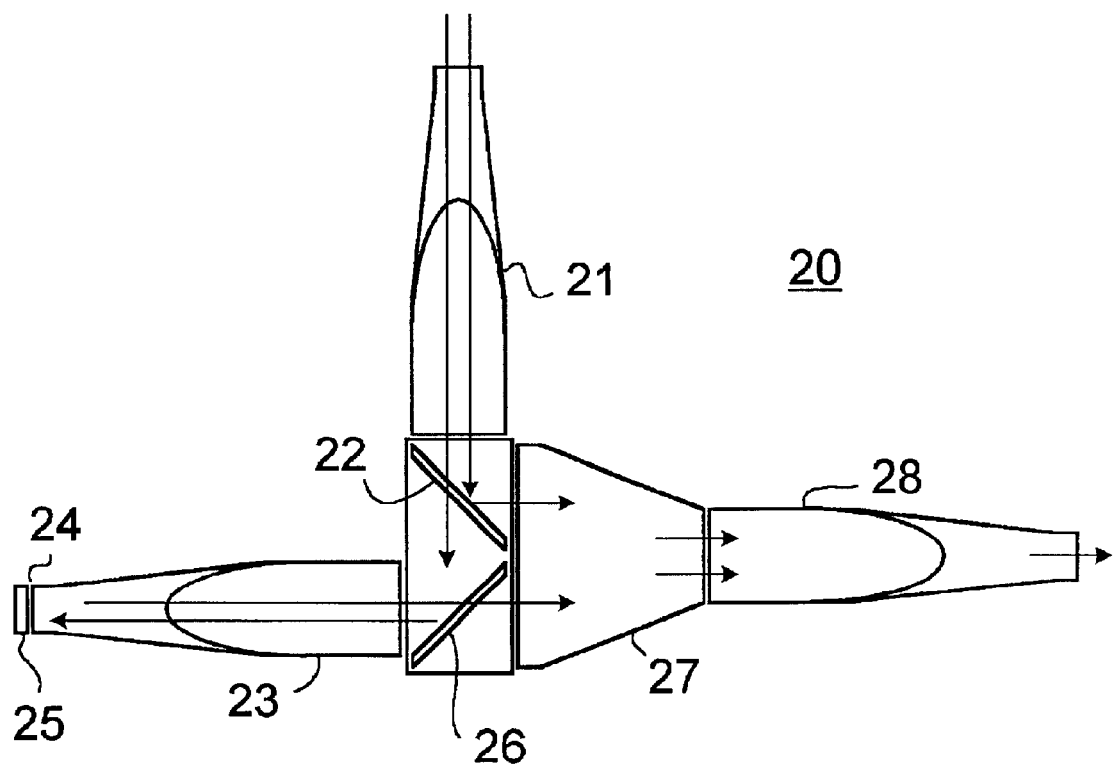
FIG. 3 depicts certain features of an ultraviolet to red converter optical component.

Referring now to FIG. 3, which depicts an ultraviolet to red converter 20 in accordance with the present invention. Light containing red, green, blue, and ultraviolet (UV) components enters a first morphing element 21 and then impinges a beam splitter refractive element 22. The beam splitter refractive element 22 reflects red, green, and blue light components while it transmits UV light. The transmitted UV light impinges a second beam splitter refractive element 26 that reflects UV light and transmits red light. The reflected UV light enters a second morphing element 23, for example a square to round morphing element, that propagates the UV light flux by total internal reflection (TIR) to a reflecting cavity 24 adjacent to the end face of the second morphing element 23 end face. The reflecting cavity 24 encloses an ultraviolet (UV) to red converting fluorescent material 25 that has an air gap between the fluorescent material and the morphing element end face. The UV light entering the reflecting cavity excites the fluorescent material thereby causing it to emit red light. The red light enters the morphing element end face and propagates back through the morphing element by TIR. The morphing element concentrates the UV light projected into the reflecting cavity and collimates the red light propagated away from the cavity. The design of the morphing element is such that it avoids TIR failure of light at its side faces and at its end face adjacent to the reflecting cavity. However, the design is such that the maximum angle of refraction of UV from the end face into the reflecting cavity air gap approaches 90 degrees. Likewise, the maximum angle of incidence on the end face of red light from the reflecting cavity also approaches 90 degrees. The morphing element end faces at air-glass interfaces can be antireflection (AR) coated to reduce fresnel reflection losses. The red light exits the morphing element through the end face and enters the UV/red beam splitter. The beam splitter transmits the red light thus propagating it to the morphing element adjacent to both beam splitters.

The morphing element also receives the red, green, and blue light reflected by the other beam splitter thereby mixing it with the red light originating at the reflecting cavity. As previously described earlier for other morphing elements, this can be designed to concentrate, collimate, or to neither concentrate nor collimate the light it propagates. Its design can ensure that TIR is not violated and it can be made long enough to make the light projected from its exit port aperture uniform spectrally, spatially, and angularly.

Figure 4:
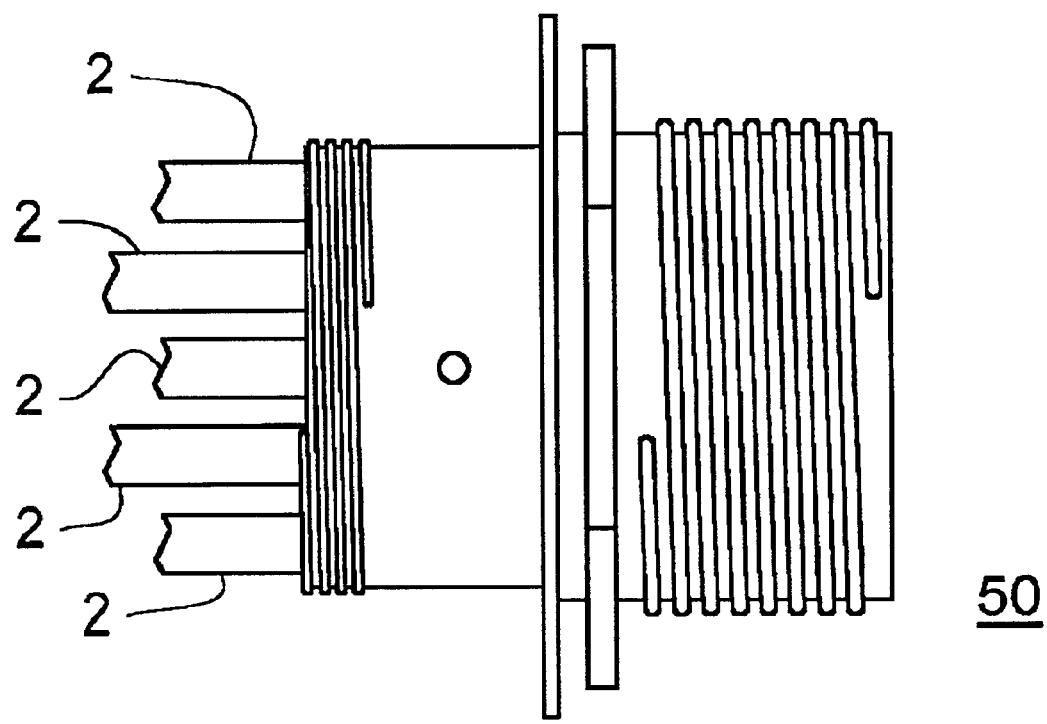
FIG. 4 depicts certain features of a combining array optical component.
Figure 4:
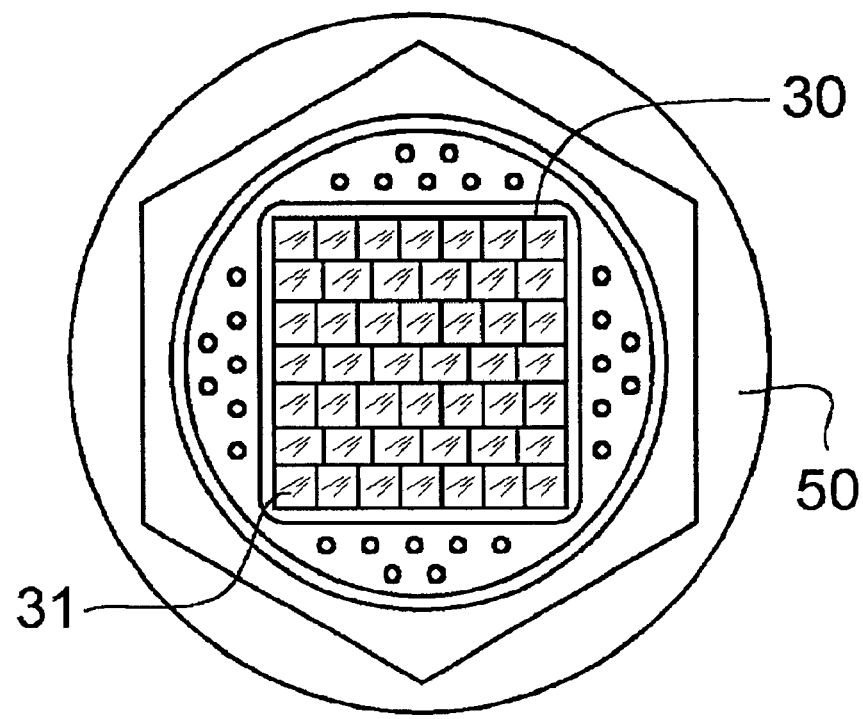

Referring next to FIG. 4, further details of the combiner array 30 are shown. The combiner array 30 is constructed from individual rectangular-to-round morphing elements 31. A staggered arrangement of its rectangular entrance port apertures, can pack efficiently to interface with a non-staggered, or regular, arrangement of square port apertures. For example, there can be forty-six (46) rectangular elements, where each rectangle has a 6:7 aspect ratio. This allows the forty-six (46) outputs from each of the collector arrays 10 to be redistributed to another number, such as twenty-five (25), of output projected image shapes 5.

Figure 7:
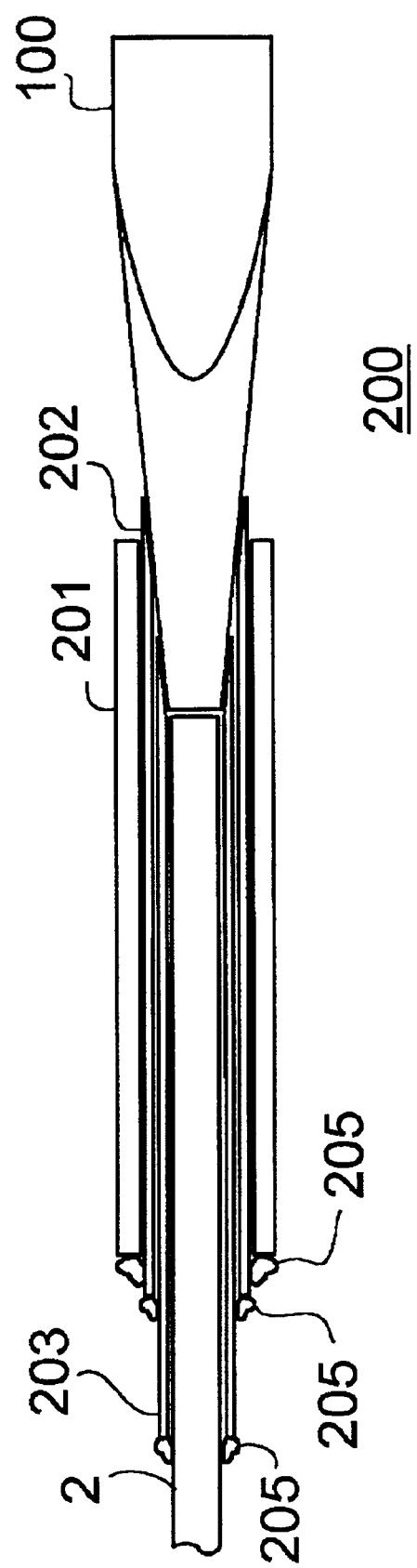
FIG. 7 depicts a cylinder to cone aligner device suitable for aligning non-imaging morphing elements, such as those shown in FIG. 6.

FIG. 4 also depicts how the optical combiner array 30 can be incorporated into an electrical connector 50 housing, such as an aircraft connector. Each of the rectangular morphing elements 31 is associated with and optically connected to a corresponding fiber optic cable 2. Further details regarding the connection between each morphing element 31 and its associated fiber optic cable are shown in FIG. 7.

Figure 5:
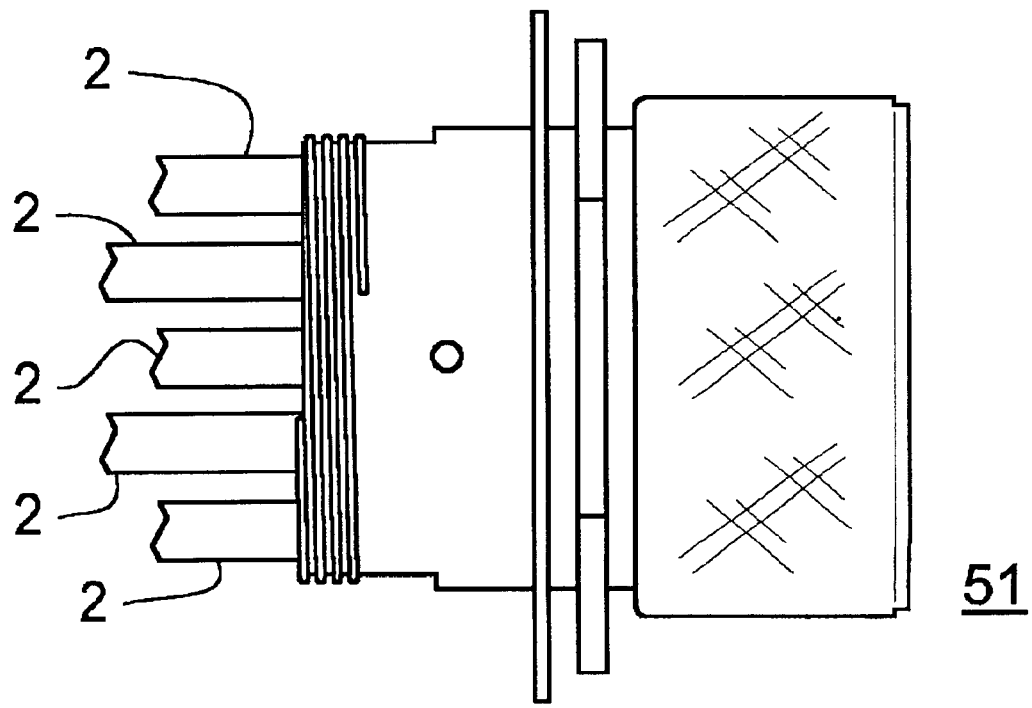
FIG. 5 depicts a mechanical connector including a distribution array optical component.
Figure 5:
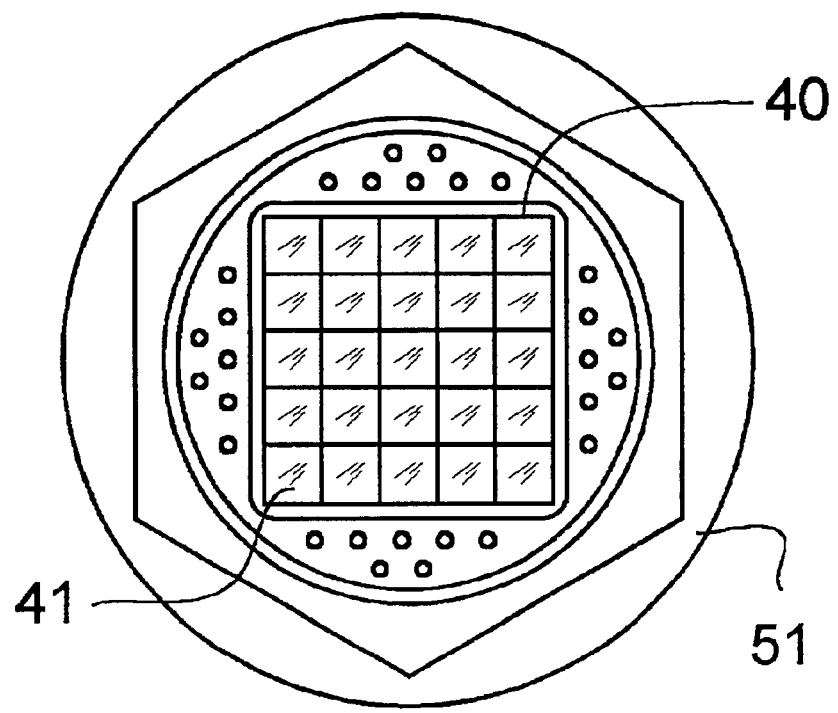

Referring next to FIG. 5, further details of the distribution array 40 are shown. The distribution array 40 is constructed from individual square-to-round morphing elements 41. The distribution array 40 is adapted to be in close optical communication with the combiner array 30, such as for example when each array is mounted in a mutually mating aircraft connector. This allows the forty-six (46) outputs from each of the collector arrays 10 to be redistributed to another number, such as twenty-five (25), of output projected image shapes 5.

FIG. 5 also depicts how the optical distribution array 40 can be incorporated into a second electrical connector 51 housing, such as an aircraft connector that mates with the first connector 50. Each of the square morphing elements 41 is associated with and optically connected to a corresponding fiber optic cable 2. Further details regarding the connection between each morphing element 31 and its associated fiber optic cable are shown in FIG. 7.

Figure 6:
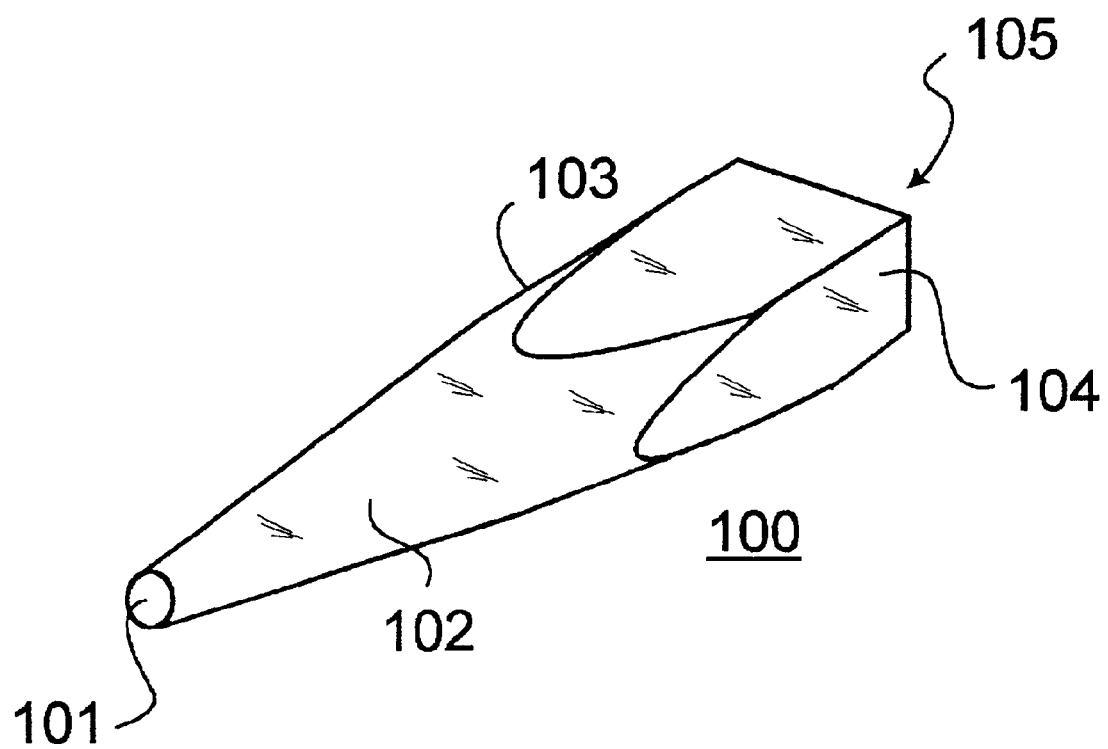
FIG. 6 is an isometric view of a single non-imaging optical morphing element suitable for use in optical components such as those shown in FIGS. 2–5.

Referring next to FIG. 6, a generic non-imaging optical morphing element 100, such as the triangular morphing element 11 of FIG. 2, the rectangular morphing element 31 of FIG. 4, or the square morphing element 41 of FIG. 5 is illustrated.

Each morphing element 100 has a uniform polygon cross-section region 104 defined by a polygonal end aperture 105, such as a square, and parallel planar surfaces. This cross-section region has the shape and sufficient length to homogenize the internally transmitted light, be efficiently nested in an array with adjacent morphing elements thereby avoiding packing fraction light losses, and facilitate accurate parallel alignment of the axes of all the array's nested elements.

Each morphing element 100 additionally has a transition region 103, where the element changes in geometric cross section from a polygon to a circle and a conical section 102 which terminates in a circular end aperture 101. The conical or cylindrical section of each morphing element can be manufactured, by example, by turning a purely polygon element about its axis on a lathe. Similarly, if a molding process is used to make the morphing element 101, the insert from which the mold components are made can be turned about its axis on a lathe.

It is important to note that the refractive index of each morphing element 100 is higher than that of air or that of an optional protective morphing element clad coating. The resulting difference in refractive indicies is sufficient to preserve total internal reflection of the light propagating within the morphing element 100. The uniform cross-section portions of the morphing elements stack together in a single closely packed array. The aperture port of the stacked array closely matches that of an adjacent single polygon element. Those skilled in the art will be able to configure many other embodiments of efficient closely packed arrays of morphing elements.

It is preferable, to the extent practical, to have radial symmetry for light that enters the fiber optic cables 2. The fiber optic cables 2 scramble the angular properties of the transmitted light rotationally about the conduit axis. This makes the angular properties of the fiber's output light rotationally symmetric. Owing to the fiber's scrambling effect, the resulting radially symmetric maximum divergence half angle of light projected from the conduit output port equals the largest of all off-axis half angles of light entering the fiber optic cable 2.

In general, a morphing element 100 should have a length equal to about ten times the largest span across its largest port. Parameters that affect the length required for a particular embodiment include:

(a) the desired output collimation angle
(b) the input collimation angle, and
(c) the refractive index of the morphing element medium.

Light efficiency loss can also be caused by a tapered section of a collimating morphing element that is too short. This occurs when the tapered section walls intercept some rays having angles of incidence too large to produce total internal reflection (TIR) thereby producing light transmission losses through these walls.

The uniformity of light projected from the port of a uniform cross-section region of a morphing element can be impaired if that region is too short. The morphing element may fail to provide adequate spatial or angular beam uniformity across the area of the its exit port aperture if its unifrom cross-section region is too short to provide sufficient spatial or angular homogenization. Ray tracing software programs such as ASAP (provided by Breault Research Organization in Tucson, Ariz.) or Light Tools (provided by Optical Research Associates in Pasadena, Calif.) can verify the performance of morphing element designs.

Preferably, morphing element 100 edges are sharp. However, for ground and polished glass morphing elements, sharp edges will have a number of chips. These chips may scatter the light they intercept. This scattered light will be decollimated and a portion of it will be lost thus causing a reduction in transmission efficiency. In addition, chips on the morphing element 100 entrance and exit apertures, 101 and 105, will reduce their effective collection and projection areas. To minimize these degradations it is preferable, to the extent practical, to minimize the size of these chips.

Scattering effects, such as that produced by edge chips, can (as mentioned above) cause decollimation of propagated light. Such decollimation can reduce light transmission efficiency. This reduced light transmission efficiency can result from light leakage through the bounding side interfaces of a light propagation element. The light leakage can be caused by failure of total internal reflection of decollimated scattered light rays at the bounding interfaces. The light rays that leak through the bounding interfaces could be absorbed in the cladding material, be transmitted into space surrounding the propagation element, or both. Even if all or a portion of the decollimated light thus generated does not leak through the bounding side interfaces, light thus decollimated will produce an undesirable increase in étendue. Other causes of scattering effects can produce a similar decollimation effect, which in turn produces similar decreases in light transmission efficiency and/or similar increases in étendue.

Refer now to FIG. 7, which shows a cylinder to cone aligner 200, aligning a fiber optic cable 2, with the circular end of a morphing element 100. In order to ensure an efficient optical coupling, the following alignment requirements exist:

(a) the two mating circular port apertures must be concentric; and
(b) the axis of the cylinder element must be parallel to and coincident with the axis of the cone element.

In order to preserve coupling efficiency, the exit port aperture of the light receiving element has a diameter smaller than that of the adjacent mating entrance port aperture of the light transmitting element. This is done to eliminate light losses due to aperture misalignments caused by the build-up of fabrication and assembly alignment errors.

In order to prevent an increase in étendue, the axis of the fiber optic cable 2 is aligned to be parallel to the axis of the conical section of the morphing element 100. If these axes are not parallel, the axis of symmetry of the beam of light emitted by the exit port of one element will enter the adjacent element at angle to its axis of symmetry. This misalignment of axes will cause the divergence angle of the light beam projected from the downstream element to increase thereby causing an undesirable increase in étendue.

The cylinder to cone aligner 200 comprises three concentric telescoping thin-walled cylindrical tubes 201, 202, and 203. The cylindrical tubes are matched to each other to produce a very close fit between the outer diameter of the next inner tube and the inner diameter of the next outer tube. The tubes are very straight to prevent jamming when the tubes slide relative to each other. The inside diameter edges of the middle tube 202 and the inner tube 203 are chamfered at their rim interface with the conical section of the morphing element 100. The chamfer angle of the resulting beveled edges is matched to a conical angle half-angle of the conical section surface.

When the chamfered faces of the inner tube 203 and middle tube 202 are both in contact with the conical surface of the morphing element 100, the axis of the inner tube 203 is parallel to and centered on the axis of the conical surface. In addition, the inside cylindrical surface of the inner tube 203 is centered on the circular port 101 of the morphing element 100.

The fiber optic cable 2 is installed in the cylinder to cone aligner 200 by sliding it the conical section of the morphing collimator 100 until it is in contact with the circular end aperture 101. This ensures the alignment of adjacent port apertures and the parallelism of the axes of the conical section and the solid core fiber. The middle tube 202 is then slid forward within the outer tube 201 until its chamfered surface is in contact with the conical section of the morphing collimator 100. Finally, the outer tube 201, middle tube 202, and inner tube 203 are all secured in their relative positions by adhesive 205.

List of Acronyms Used in the Specification

The following is a list of the acronyms used in the specification in alphabetical order.

| | |
|---|---|
| HID | high intensity discharge (lamp) |
| LGE | light generation enclosure |
| TIR | total internal reflection |
| UV | ultraviolet (light) |

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A cylinder to cone aligner (200) device for aligning the apertures and axes of symmetry of a solid cylindrical element (2) and an element (100) including a conical section where the apertures of said solid cylindrical element and said conical section are substantially normal to the corresponding axes of symmetry of said solid cylindrical element and said conical section, said cylinder to cone aligner comprising:
   (a) as outer tube (201);
   (b) a middle hollow cylindrical tube (202) including beveled edges on its inner cylindrical surface, said beveled edges being matched to a conical half-angle of said conical section;
   (c) an inner hollow cylindrical tube (203) including an outer cylindrical surface that is a close fit match to the inner cylindrical surface of said middle hollow cylindrical tube and beveled edges on its inner cylindrical surface, said beveled edges being matched to a conical half-angle of said conical section; wherein
   (d) the apertures and axes of said solid cylindrical element and said conical section can be aligned by
      (i) engaging the conical surface of said conical cross section simultaneously with the beveled edges of both the middle and the inner hollow cylindrical tubes,
      (ii) inserting the cylindrical element into the inner cylindrical opening of the inner hollow tube, and
      (iii) sliding the cylindrical element into the opening until its aperture engages the aperture of the conical section.

2. A system for distributing light comprising:
   a plurality of light generation enclosures (1):
   a plurality of collector arrays (10), each one of the collector arrays corresponding to one of said light generation enclosures and providing a light output;
   a plurality of ultraviolet to red converters (20), each of said ultraviolet to red converters receiving light containing an ultraviolet component and converting a substantial portion of said ultraviolet component into visible light;
   a plurality of combiner arrays (30), each connected to a plurality of said converters;
   a plurality of distribution arrays, each one in optical communication with said combiner arrays and providing a plurality of light outputs; and
   a plurality of projection lenses (4), each one of said projection lenses adapted to receive one of said plurality of light outputs from one of said distribution arrays; and wherein each of said optical collector arrays comprises:
   a plurality of triangular to round morphing elements (11) arranged in a closely packed hexagonal array within a hexagonal shaped hollow central region (12); and
   wherein each of said triangular to round morphing elements further comprises
   a substantially circular end aperture (101),
   a conical section (102) that transitions in geometric cross section over a first length from said small substantially circular end aperture to a large circular cross section,
   a transition region (103) that transitions in geometric cross section over a second length from said large circular cross section to a larger triangular cross section, and
   an area of constant triangular cross section (104) having a third length where said larger triangular cross section is constant, thereby forming planar side surfaces and terminating in a triangular end aperture (105), wherein said triangular end aperture is distally opposed from said small substantially circular end aperture.

3. The system for distributing light in accordance with claim 2 wherein said plurality of triangular to round morphing elements numbers forty-six triangular to round morphing elements.

4. A system for distributing light comprising:
   a plurality of light generation enclosures (1);
   a plurality of collector arrays (10), each one of the collector arrays corresponding to one of said light generation enclosures and providing a light output;
   a plurality of ultraviolet to red converters (20), each of said ultraviolet to red converters receiving light containing an ultraviolet component and converting a substantial portion of said ultraviolet component into visible light;
   a plurality of combiner arrays (30), each connected to a plurality of said converters;
   a plurality of distribution arrays, each one in optical communication with said combiner arrays and providing a plurality of light outputs; and
   a plurality of projection lenses (4), each one of said projection lenses adapted to receive one of said plurality of light outputs from one of said distribution arrays; and wherein each of said optical combiner arrays comprises;
   a plurality of rectangular to round morphing elements (31) arranged in a closely packed square shaped array; and
   wherein each of said rectangular to round morphing elements further comprises
   a small substantially circular end aperture (101),
   a conical section (102) that transitions in geometric cross section over a first length from said small substantially circular end aperture to a larger circular cross section; and
   a transition region (103) that transitions in geometric cross section over a second length from said large circular cross section to a larger rectangular cross section, and an area of constant triangular cross section (104) having a third length where said larger triangular cross section is constant, thereby forming planar side surfaces and terminating in a rectangular end aperture (105), wherein said rectangular end aperture is distally opposed from said small substantially circular end aperture.

5. The system for distributing light in accordance with claim 4 wherein said plurality of rectangular to round morphing elements number forty six rectangular to round morphing elements.

6. The system for distributing light in accordance with claim 4 further comprising
   (a) an electrical connector shell (50), and
   (b) wherein said closely packed square shaped array is mounted within said electrical connector shell and adapted to optically communicate with a corresponding optical array mounted within a corresponding mating electrical connector shell (51).

7. A system for distributing light comprising:
   a plurality of light generation enclosures (1);
   a plurality of collector arrays (10), each one of the collector arrays corresponding to one of said light generation enclosures and providing a light output;
   a plurality of ultraviolet to red converters (20), each of said ultraviolet to red converters receiving light containing an ultraviolet component and converting a substantial portion of said ultraviolet component into visible light;
   a plurality of combiner arrays, each connected to a plurality of said converters;
   a plurality of distribution arrays, each one in optical communication with said combiner arrays and providing a plurality of light outputs, and
   a plurality of projection lenses (4), each one of said projection lenses adapted to receive light from one of said plurality of light outputs from one of said distribution arrays, and
   wherein each of said optical distribution arrays further comprises
   a small substantially circular end aperture (101),
   a conical section (102) that transitions in geometric cross section over a first length from said small substantially circular end aperture to a larger circular cross section,
   a transition region (103) that transitions in cross section over a second length from said large circular cross section to a larger square cross section, and
   an area of constant square cross section (104) having a third length where said larger cross section is constant and terminating in a square end aperture (105), wherein said square end aperture is distally opposed from said small substantially circular end aperture.

8. The system for distributing light in accordance with claim 7 wherein said plurality of square to round morphing elements numbers twenty-five square to round morphing elements.

9. The system for distributing light in accordance with claim 7 wherein each of said optical distribution arrays further comprises
   (a) an electrical connector shell (51); and
   (b) wherein said closely packed square shaped array is mounted within said electrical connector shell and adapted to optically communicate with a corresponding optical array mounted within a corresponding mating electrical connector shell (50).

10. A system for distributing light comprising:
    (a) a plurality of light generation enclosures (1);
    (b) a plurality of optical collector arrays (10), each one of the optical collector arrays corresponding to one of said light generation enclosures and providing a light output, and further comprising
       (i) a plurality of triangular to round morphing elements (11) arranged in a closely packed hexagonal shaped array with a hexagonal shaped hollow central region (12); and
       (ii) wherein each of said triangular to round morphing elements further comprises
          (A) a small substantially circular end aperture (101),
          (B) a conical section (102) that transitions in geometric cross section over a first length from said small substantially circular end aperture to a larger circular cross section,
          (C) a transition region (103) that transitions in geometric cross section over a second length from said large circular cross section to a larger triangular cross section, and
          (D) an area of constant triangular cross section (104) having a third length where said larger triangular cross section is constant, thereby forming planar side surfaces and terminating in a triangular end aperture (105), wherein said triangular end aperture is distally opposed from said small substantially circular end aperture;
    (c) a plurality of combiner arrays (30) each connected to a plurality of said converters;
    (d) a plurality of distribution arrays, each one in optical communication with said combiner arrays and providing a plurality of light outputs; and
    (e) a plurality of projection lens (4), each one of said projection lenses adapted to receive one of said light outputs from one of said distribution arrays.

11. The system for distributing light in accordance with claim 10 wherein said plurality of triangular to round morphing elements numbers forty-six triangular to round morphing elements.

12. A system for distributing light comprising:
    (a) a plurality of light generation enclosures (1);
    (b) a plurality of optical collector arrays (10), each one of the optical collector arrays corresponding to one of said light generation enclosures and providing a light output;
    (c) a plurality of combiner arrays (30), each connected to a plurality of said converters, and further comprising
       (i) a plurality of rectangular to round morphing elements (31) arranged in a closely packed square shaped array; and
       (ii) wherein each of said rectangular to round morphing elements further comprises
          (A) a small substantially circular end aperture (101),
          (B) a conical section (102) that transitions in geometric cross section over a first length from as small substantially circular end aperture to a larger circular cross section, and
          (C) a transition section (103) that transitions in cross section over a second length from said large circular cross section to a larger rectangular cross section, and
          (D) an area of constant triangular cross section (104) having a third length where said larger triangular cross section is constant, thereby forming planar side surfaces and terminating in a rectangular end aperture 105), wherein said rectangular end aperture is distally opposed from said small substantially circular end aperture;

(d) a plurality of distribution arrays, each one in optical communication with said combiner arrays and providing a plurality of light outputs; and (e) a plurality of projection lenses (4), each one of said projection lenses adapted to receive one of said plurality of light outputs from one of said distribution arrays.

13. The system for distributing light in accordance with claim 12 wherein said plurality of rectangular to round morphing elements number forty-six rectangular to round morphing elements.

14. The system for distributing light in accordance with claim 12 further comprising (a) an electrical connector shell (50), and (b) wherein said closely packed square shaped array is mounted within said electrical connector shell and adapted to optically communicate with a corresponding optical array mounted within a corresponding mating electrical connector shell (51).

15. A system for distributing light comprising:

(a) a plurality of light generation enclosures (1);

(b) a plurality of optical collector arrays (10), each one of the optical collector arrays corresponding to one of said light generation enclosures and providing a light output;

(c) a plurality of combiner arrays (30), each connected to a plurality of said converters;

(d) a plurality of distribution arrays (40), each one in optical communication with said combiner arrays and providing a plurality of light outputs, and further comprising (i) a plurality of square to round morphing elements (41) arranged in a closely packed square shaped array; and (ii) wherein each of said square to round morphing elements further comprises (A) a substantially circular end aperture (101), (B) a conical section (102) that transitions in geometric cross section over a first length from said small substantially circular end aperture to a large circular cross section, (C) a transition region (103) that transitions in cross section over a second length from said large circular cross section to a larger square cross section, and (D) an area of constant square cross section (104) having a third length where said larger cross section is constant and terminating in a square end aperture (105), wherein said square end aperture is distally opposed from said small substantially circular end aperture; and (e) a plurality of projection lenses (104) each one of said projection lenses adapted to receive one of said plurality of light outputs from one of said distribution arrays.

16. The system for distributing light in accordance with claim 15 wherein said plurality of square to round morphing elements numbers twenty-five square to round morphing elements.

17. The system for distributing light in accordance with claim 15 wherein each of said optical distribution arrays further comprises (a) an electrical connector shell (51); and (b) wherein said closely packed square shaped array is mounted within said electrical shell and adapted to optically communicate with a corresponding optical array mounted within a corresponding mating electrical connector shell (50).

* * * * *